United States Patent [19]

Vogt

[11] 4,123,532

[45] Oct. 31, 1978

[54] METHOD FOR TREATMENT OF ASTHMA

[75] Inventor: B. Richard Vogt, Yardley, Pa.

[73] Assignee: E. R. Squibb & Sons, Inc., Princeton, N.J.

[21] Appl. No.: 781,618

[22] Filed: Mar. 28, 1977

[51] Int. Cl.$^2$ .......................................... A61K 31/505
[52] U.S. Cl. ................................................... 424/251
[58] Field of Search .................. 424/251; 260/256.4 F

[56] References Cited

U.S. PATENT DOCUMENTS

| | | | |
|---|---|---|---|
| 3,313,815 | 4/1967 | Wolfe et al. ................... | 260/256.4 F |
| 3,897,434 | 7/1975 | Katner .......................... | 260/256.4 Q |

OTHER PUBLICATIONS

Physicians Desk Reference, 1974 ed., pp. 760–761.

*Primary Examiner*—Leonard Schenkman
*Attorney, Agent, or Firm*—Lawrence S. Levinson; Merle J. Smith; Burton Rodney

[57] ABSTRACT

A method is provided for treatment of asthma by administering to a mammalian host a pyrazolo[1,5-c]quinazolin-5(6H)-one of the structure

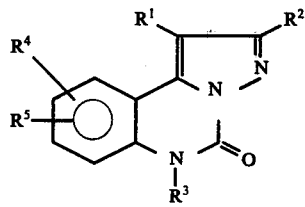

wherein $R^1$ is hydrogen, lower alkyl, lower alkoxycarbonyl, phenyl optionally substituted with halogen, lower alkyl or lower alkoxy, $R^2$ is carboxy, lower alkoxycarbonyl, alkoxy, hydrogen, benzoyl optionally substituted with halogen, lower alkyl or lower alkoxy, and $R^3$, $R^4$ and $R^5$ are as defined hereinafter, the above compound preferably being carried by a physiologically acceptable pharmaceutical carrier.

7 Claims, No Drawings

METHOD FOR TREATMENT OF ASTHMA

FIELD OF THE INVENTION

The present invention relates to a method of treating asthma in mammalian hosts by administering a pyrazolo[1,5-c]-quinazolin-5(6H)-one.

BACKGROUND OF THE INVENTION

U.S. Pat. No. 3,897,434 to Katner assigned to Eli Lilly and Company discloses various pyrazolo[1,5-c]-quinazolin-5(6H)-ones as being useful as anti-inflammatory agents, immunosuppressants or complement inhibitors. Katner indicates that some of the pyrazolo[1,5-c]quinazolin-5(6H)-ones of the structure

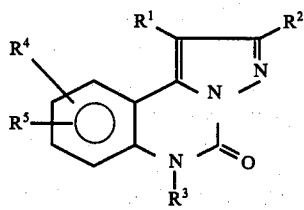

wherein $R^1$ is hydrogen or $C_1$-$C_3$-alkoxycarbonyl; $R^2$ is $C_1$-$C_3$ alkoxycarbonyl, acetyl, benzoyl or monosubstituted benzoyl in which the substituent is fluoro, chloro, bromo, $C_1$-$C_3$ alkyl, or $C_1$-$C_3$ alkoxy; and $R^3$ is hydrogen, methyl, benzyl, or monosubstituted benzyl in which the substituent is fluoro, chloro or bromo; with the limitation that when $R^1$ is hydrogen and $R^2$ is $C_1$-$C_3$ alkoxycarbonyl, $R^3$ cannot be methyl, have the ability to suppress immune mechanisms in a host mammal as measured by the compound's activity as an anti-allergic agent.

"Immunosuppressant activity" is the property of a compound to inhibit the immune response of an animal to a specific antigen. Indeed, the procedure outlined in the Katner patent for testing of immunosuppressant activity involves the intraperitoneal injection of antigen (sheep red blood cells) into a group of mice that are subsequently treated for a period of time. The animals are bled on the seventh day after injection with antigen and the antibody titer in control and test animals are compared.

"Anti-allergic activity" is normally demonstrated by the passive cutaneous anaphylaxis reaction in rats. The skin of rats is first sensitized by the intradermal injection of reaginic (allergic) antibody. Twenty-four hours later, the animals receive a challenge injection of antigen together with Evan's blue dye given intravenously. The antigen, thus injected directly into the circulation, encounters the antibody in the skin and an "allergic reaction" occurs which is identified by the formation of intracutaneous edema. The edema is marked by the presence of the Evan's blue dye in the circulation. Test compounds are evaluated by their ability to prevent or diminish the amount of edema found as a result of inhibiting some phase of the allergic reaction.

Thus, the allergic reaction does not involve antibody formation as is observed for immunosuppressive activity. Likewise, immunosuppressive activity does not involve the formation of the allergic reaction. They are two distinct activities. Thus, anti-allergic activity is not a measure of a compound's activity as an immunosuppressant and vice versa. Furthermore, the fact that a compound has immunosuppressant activity does not make it predictable that it will have anti-allergy activity, and vice versa. However, it has been unexpectedly discovered that the pyrazolo[1,5-c]-quinazolin-5(6H)-ones described herein have anti-allergenic activity and are useful in the treatment of asthma.

DETAILED DESCRIPTION OF THE INVENTION

The method of the present invention resides in the treatment of asthma by administering to a mammalian host a pyrazolo[1,5-c]quinazolin-5(6H)-one (such as defined in U.S. Pat. No. 3,897,434 to Katner) having the structure

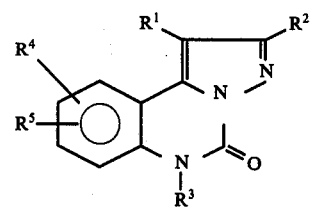

wherein $R^1$ is hydrogen, lower alkyl, lower alkoxycarbonyl, phenyl optionally substituted with halogen (F, Cl, Br), lower alkyl or lower alkoxy; $R^2$ is hydrogen, carboxy, lower alkyl, lower alkoxycarbonyl, acetyl, benzoyl optionally substituted with halogen (F, Cl, Br), lower alkyl or lower alkoxy; $R^3$ is hydrogen, lower alkyl, benzyl, phenyl, and benzyl or phenyl optionally substituted with lower alkyl, trifluoromethyl, lower alkoxy, halogen (F, Cl or Br), or methylsulfonyl; $R^4$ and $R^5$ may be the same or different and may be hydrogen, lower alkyl, lower alkoxy, F, Cl or Br.

Unless otherwise indicated the term "lower alkyl" or "alkyl" as employed herein includes both straight and branched chain radicals of up to eight carbon atoms, for instance, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, and the like.

Unless otherwise indicated the term "lower alkoxy" or "alkoxy" includes straight and branched chain radicals which correspond to the above lower alkyl groups attached to an oxygen atom.

Unless otherwise indicated, the term "lower alkoxycarbonyl" or "alkoxycarbonyl" as employed herein includes any of the above lower alkyloxy groups linked via the oxygen atom to a carbonyl group.

The above compounds employed in carrying out the method of the invention may be prepared by a variety of techniques as disclosed in U.S. Pat. No. 3,897,434 to Katner, the disclosure of which is incorporated herein by reference.

Starting materials or final products that are mixtures of isomers can be separated into the single isomers by methods in themselves known, e.g., by fractional distillation, crystallization and/or chromatography. Racemic products can likewise be resolved into the optical antipodes, for example by separation of diastereomeric salts thereof, e.g., of the fractional crystallization, in the case of basic compounds, of d- or l-tartrates, maleates, -mandelates, -N-acetylphenylalaninates or -camphor sulfonates, or, in the case of acid compounds, d- or l-α-methylbenzylamine and reconverting the diastereomeric salts into the free antipodes.

Certain of the compounds of formula I may form physiologically acceptable acid-addition salts or base addition salts with inorganic and organic acids or alkali metal or alkaline earth metal bases such as sodium hydroxide or calcium hydroxide. These salts frequently provide useful means for isolating the products from reaction mixtures by forming the salt in a medium in which it is insoluble. The free base may then be obtained by neutralization, e.g., with a base or acid. Then any other salt may again be formed from the free base and the appropriate inorganic acid or base. Illustrative are the hydrohalides, especially the hydrochloride and hydrobromide which are preferred, sulfate, nitrate, phosphate, oxalate, tartrate, maleate, fumarate, citrate, succinate, methanesulfonate, benzenesulfonate, toluenesulfonate, and the like.

In accordance with the method of the present invention, the compounds of formula I, and their pharmaceutically acceptable salts, are useful in treating various allergic (asthmatic) conditions in mammalian species such as humans, mice, cats, dogs, etc., when administered in amounts ranging from about 0.1 milligram to about 500 milligrams per kilogram of body weight per day. The compounds can be used prophylactically to treat asthma, hay-fever, and rhinitis. A preferred dosage regimen would be from about 0.5 milligrams to about 200 milligrams per kilogram of body weight per day administered in a single dose or plurality of divided doses.

The compounds of formula I, and the pharmaceutically acceptable salts thereof, are anti-asthmatics which inhibit the effects of certain antigen-antibody reactions and in particular inhibit the release of mediators such as histamine. The anti-asthmatic activity of these compounds is determined by the reaginic antibody-induced passive cutaneous anaphylaxis (PCA) reaction in rats. (See Bach, Immediate Hypersensitivity: Laboratory Models and Experimental Findings, Ann. Rep. Med. Chem., 7: 238-248 (1972), for a discussion of the predictability of clinical efficacy of compounds active in the PCA).

A compound of formula I, or a salt thereof, can be administered by the inhalation of an aerosol or powder as described in U.S. Pat. No. 3,772,336 (i.e., breathing finely divided particles of the active ingredient into the lungs), orally or parenterally (for example, intraperitoneally, subcutaneously, intramuscularly or intravenously). Powders can be prepared by comminuting the active ingredient with a similarly comminuted diluent such as starch or lactose. Suitable forms for oral administration include capsules, tablets, troches, elixirs, wafer, chewing gum, syrups, and a suitable form for parenteral administration in a sterile injectable. Such unit dosage forms are prepared by compounding with a conventional vehicle, excipients, binders, preservatives, stabilizers, flavoring agents or the like as called for by acceptable pharmaceutical practice. Also, the compounds used in this invention can be formulated with other pharmaceutically active compounds such as bronchodilators, steroids, antihistamines, etc.

The tablets, troches, pills, capsules and the like may also contain the following: a binder such as gum tragacanth, acacia, corn starch or gelatin; an excipient such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following Examples further illustrate and represent preferred embodiments of the invention. All temperatures are expressed in degrees Centigrade.

EXAMPLE 1

5,6-Dihydro-5-oxopyrazolo[1,5-c]quinazoline-2-carboxylic acid, ethyl ester

A solution of 48 g (0.30 mole) of 3-diazooxindole and 38.7 g (0.39 mole) of ethyl propiolate in 2 l. of benzene is refluxed overnight. The reaction mixture is cooled to room temperature and the crude product filtered, wt.=60 g. Crystallization from absolute ethanol gives 54 g, m.p. 242°–244° (Sl. d.).

An analytical sample is prepared by taking a 10 g aliquot of the above material and recrystallizing three times with absolute ethanol, m.p. 253°–254° (Sl. d.), 3.9 g.

EXAMPLE 2

Passive Cutaneous Anaphylaxis (PCA) Test of 5,6-Dihydro-5-oxopyrazolo[1,5-c]quinazoline-2-carboxylic acid, ethyl ester In this test, 0.05 ml of appropriately diluted whole rat serum containing IgE antibody is injected intradermally into the skin of a rat. The next day, the animals are dosed with the test compound ten minutes prior to the i.v. challenge injection of antigen and Evan's blue dye. Thirty minutes later, the animals are sacrificed, the skin reflected and the reaction quantitated by measuring the dye-marked edema and scoring the color intensity of the reaction.

The results of rat PCA testing are shown in Table I below and indicate that the test compound has anti-asthma activity.

TABLE I

Results of Testing of 5,6-Dihydro-5-oxopyrazolo[1,5-c]quinouzoline-2-carboxylic acid, ethyl ester

| | | |
|---|---|---|
| A. $ID_{50}$, mg/kg, rats dosed ten min. prior to challenge | IP(interperitoneally) PO(orally) | 2 3 |
| B. Maximum % inhibition rats dosed ten min. prior to challenge | IP | 94% (10 mg/kg) |
| | PO | 95% (9 mg/kg) |

EXAMPLE 3

Parenteral Composition Containing 5,6-Dihydro-5-oxopyrazolo-[1,5-c]quinazoline-2-carboxylic acid A suspension of 25.7 g (0.10 mole) of 5,6-dihydro-5-oxopyrazolo[1,5-c]quinazoline-2-carboxylic acid, ethyl ester (prepared as described in Example 1) in 2.5 l. of 10% alcoholic potassium hydroxide is refluxed for 3 hours. The thick suspension is cooled to room temperature and filtered. The solid is dissolved in water and extracted with chloroform. After treatment with Norit-A and filtering, the aqueous solution is cooled in an ice bath and acidified (Congo red) with 25 ml of concentrated hydrochloric acid. The white precipitate is filtered and then digested with 1 l. of hot water. The suspension is filtered and the solid dried to give 20.0 g of product, m.p. 284°–285° (d).

A dispersion suitable for parenteral administration is prepared by dispersing 1 mg of 5,6-dihydro-5-oxopyrazolo-[1,5-c]quinazoline-2-carboxylic acid in about 100 ml of water for injection.

EXAMPLE 4

Parenteral Composition Containing Pyrazolo[1,5-c]quinazolin-5(6H)-one

Twelve grams of 5,6-dihydro-5-oxopyrazolo[1,5-c]-quinazoline-2-carboxylic acid is put into a 250 ml single neck round bottom flask, and stirred with a magnetic stirrer under a nitrogen atmosphere. The flask and contents are immersed in a silicone oil bath which is then heated to 285°. After 0.5 hour, the melt is removed from the bath and allowed to solidify. The crude solid is then pulverized and purified by high vacuum sublimation. The sublimate is recrystallized from methanol to give 7.0 g of the title compound, m.p. 253°–254°.

A dispersion suitable for parenteral administration is prepared by dispersing 1 mg of pyrazolo[1,5-c]quinazolin-5(6H)-one in about 100 ml of water for injection.

The above compound is subjected to rat PCA testing as described in Example 2. The following results are obtained which indicate that the test compound has anti-asthma activity.

TABLE II
Results of Testing of Pyrazolo[1,5-c]quinazoline-5(6H)-one

| Maximum % inhibition | IP (75 mpk) | 59 |
|---|---|---|
| rats dosed ten min. prior to challenge | | |

EXAMPLE 5

Parenteral Composition Containing 5,6-Dihydro-5-oxo-2-phenylpyrazolo[1,5-c]quinazoline-1-carboxylic acid, ethyl ester A suspension of 9.6 g (0.060 mole) of 3-diazooxindole in 200 ml of xylene is treated with 12 g (0.068 mole) of 92% ethyl phenyl propiolate and the mixture refluxed for 96 hours.

On cooling to room temperature, a solid is formed, which is filtered (10 g). This is crystallized once from ethyl acetate and twice from absolute ethanol to yield 4.5 g of analytically pure title compound, m.p. 235°–237°.

A dispersion suitable for parenteral administration is prepared by dispersing 1 mg of 5,6-dihydro-5-oxo-2-phenylpyrazolo[1,5-c]quinazoline-1-carboxylic acid, ethyl ester in about 100 ml of water for injection.

The above compound is subjected to rat PCA testing as described in Example 2. The following results are obtained which indicate that the test compound has anti-asthma activity.

TABLE III
Results of Testing of 5,6-Dihydro-5-oxo-2-phenyl-pyrazolo[1,5-c]quinazoline-1-carboxylic acid, ethyl ester

| Maximum % inhibition | IP (75 mpk) | 42 |
|---|---|---|
| rats dosed ten min. prior to challenge | | |

EXAMPLE 6

Parenteral Composition Containing 5,6-Dihydro-5-oxopyrazolo-[1,5-c]quinazoline-2-carboxylic acid, methyl ester A solution of 4.8 g (0.030 mole) of 3-diazooxindole and 3.36 g (0.040 mole) of methyl propiolate in 200 ml of benzene is refluxed overnight. The reaction mixture is cooled to room temperature and the crude product filtered (4.9 g). Three recrystallizations from methanol gives 3.2 g of analytically pure material, m.p. 295°–297° (d) with softening at 290°.

A dispersion suitable for parenteral administration is prepared by dispersing 1 mg of 5,6-dihydro-5-oxopyrazolo-[1,5-c]quinazoline-2-carboxylic acid, methyl ester in about 100 ml of water for injection.

EXAMPLE 7

Tablets Containing 5,6-Dihydro-5-oxopyrazolo[1,5-c]-quinazoline-2-carboxylic acid, n-propyl ester 2.0 g (0.0126 mole) of 3-diazo-oxindole and 1.7 g (1.2 equivalents) of n-propyl propiolate are dissolved in xylene (85 ml) and refluxed under nitrogen for 24 hours. The dark reddish-brown precipitates are filtered off, washed with ether and dried. Yield: 1.5 g, 43.86% yield.

The crude product is impregnated in a small amount of silica gel, placed at the top of a silica gel column (60 g) and the column eluted successively with pentane (150 ml), pentane:ether (1:1, 800 ml), ether (700 ml), ether:-chloroform (2:1, 300 ml), chloroform (200 ml), chloroform:ethyl acetate (8:2, 200 ml), and ethyl acetate: chloroform (1:1, 1.0 liters), collecting fractions with a fraction collector. The fractions containing the desired product are combined, stripped to dryness and the crude material recrystallized from a minimal amount of ethanol. Yield: 700 mg; m.p. 229°–230°, light peach-colored material. Trituration of the product with ~20 ml hot methylene chloride gives 574 mg of white precipitates, m.p. 231°–233°.

The following ingredients are used to make 1,000 200 mg tablets each containing 100 mg of active ingredient:

| | |
|---|---|
| 5,6-Dihydro-5-oxo-pyrazolo[1,5-c]-quinazoline-2-carboxylic acid, n-propyl ester | 100 gm. |
| Polyvinyl pyrrolidone | 7.5 gm. |
| Lactose | 20 gm. |
| Magnesium stearate | 3.5 gm. |
| Corn starch | 17.5 gm. |
| Avicel (microcrystalline cellulose) | 51.5 gm. |

The medicament and lactose are thoroughly admixed. The polyvinyl pyrrolidone is dissolved in ethanol USP to make a 30% solution. This solution is used to granulate the mixture of medicament and lactose. The granulation is passed through a No. 16 screen and air dried. The dried granulation is then passed through a No. 20 screen. To the screened granulate are added the magnesium stearate, Avicel and the corn starch and the mixture is blended. The blend is then compressed into 200 mg tablets on a standard concave punch. The tablets are then veneer coated with methyl cellulose in a spray pan.

EXAMPLE 8

Tablets Containing 5,6-Dihydro-5-oxopyrazolo[1,5-c]-quinazoline-2-carboxylic acid, n-butyl ester 2.0 g (0.126 mole) of 3-diazo-oxindole is taken up in xylene (85 ml), treated with 1.2 equivalents of n-butyl propiolate (1.9 g) and refluxed under a stream of nitrogen for 17 hours in an oil bath. The light coral-colored precipitates that form are cooled and filtered off and washed with ether. Yield: 3.0 g, m.p. 190°-195°; 83.57% crude yield. The crude product is taken up in boiling absolute ethanol (250 ml), treated with activated carbon, filtered and concentrated down on a steam bath to a volume of ~75 ml. After cooling, tan-colored precipitates are filtered off and dried in a vacuum oven at room temperature for 4 hours. Yield: 2.2 g, m.p. 198°-200°.

The following ingredients are used to make 1,000 200 mg tablets each containing 100 mg of active ingredient:

| | |
|---|---|
| 5,6-Dihydro-5-oxopyrazolo[1,5-c]-quinazoline-2-carboxylic acid, n-butyl ester | 100 gm. |
| Polyvinyl pyrrolidone | 7.5 gm. |
| Lactose | 20 gm. |
| Magnesium stearate | 3.5 gm. |
| Corn starch | 17.5 gm. |
| Avicel (microcrystalline cellulose) | 51.5 gm. |

The medicament and lactose are thoroughly admixed, the polyvinyl pyrrolidone is dissolved in ethanol USP to make a 30% solution. This solution is used to granulate the mixture of medicament and lactose. The granulation is passed through a No. 16 screen and air dried. The dried granulation is then passed through a No. 20 screen. To the screened granulate are added the magnesium stearate, Avicel and the corn starch and the mixture is blended. The blend is then compressed into 200 mg. tablets on a standard concave punch. The tablets are then veneer coated with methyl cellulose in a spray gun.

The above compound is subjected to rat PCA testing as described in Example 2. The following test results are obtained which indicate that the test compound has anti-asthma activity.

TABLE IV

Results of Testing of 5,6-Dihydro-5-oxopyrazolo[1,5-c]quinazoline-2-carboxylic acid, n-butyl ester

| | | | |
|---|---|---|---|
| A. $ID_{50}$, mg/kg, rats dosed ten min. prior to challenge | IP | | 9 |
| B. Maximum % inhibition rats dosed ten min. prior to challenge | IP (150 mpk) | | 78% (10 mg/kg) |

EXAMPLE 9

Oral Syrup Containing 5,6-Dihydro-1-methyl-5-oxopyrazolo-[1,5-c]quinazoline-2-carboxylic acid, ethyl ester A solution of 4.8 g (0.030 mole) of 3-diazooxindole in 350 ml of xylene is treated with 3.7 g (0.033 mole) of ethyl tetrolate and refluxed for 48 hours under nitrogen. The reaction mixture is stripped to a dark residue of 8.0 g which is chromatographed on a 160 g dry silica gel column. Elution with 500 ml of ether followed by 2 liters of chloroform-methanol mixture (95:5) affords 7.0 g of solid. This is digested with 250 ml of boiling dichloromethane to give 5.5 g (68% direct yield). The material is treated subsequently to remove a persistent colored contaminant. Recrystallization from 250 ml of dichloromethane-methanol (50:1) gives 4.8 g; digestion with dichloromethane followed by digestion with ethyl acetate and finally recrystallization from methanol-chloroform (20:1) gives 4.2 g of white, analytically pure material, m.p. 218°-220°.

An oral syrup is prepared as described below.

| Oral Syrup Formulation | |
|---|---|
| Ingredient | Amount |
| 5,6-Dihydro-1-methyl-oxopyrazolo-[1,5-c]quinazoline-2-carboxylic acid, ethyl ester | 500 mg |
| Sorbitol solution (70% N.F.) | 40 ml |
| Sodium benzoate | 150 mg |
| Sucaryl | 90 mg |
| Saccharin | 10 mg |
| Red Dye (F.D.& Co. No. 40) | 10 mg |
| Cherry flavor | 50 mg |
| Distilled water  qs. to | 100 ml |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

EXAMPLE 10

Oral Syrup Containing 9-Chloro-5,6-dihydro-5-oxopyrazolo[1,5-c]quinazoline-2-carboxylic acid, ethyl ester I. Preparation of 5-chloro-isatin Reference: German Patent #2158955

One hundred and forty-seven grams (1 mole) of isatin is added to 830 ml of nitrobenzene containing 5 ml of pyridine. The suspension is warmed to 55° and sulfuryl chloride (160 g, 1.18 mole) added dropwise over a 1 hour period after which the reaction mixture is stirred 0.5 hour longer at 55°. The solid is filtered, washed with toluene and air dried to give 160 g (88%), m.p. 242-245°. Recrystallization from 95% ethanol gives 150 g, m.p. 246°-248°.

II. Preparation of 3-p-Tosylhydrazone of 5-chloro-isatin

Forty grams (0.22 mole) of 5-chloro-isatin is dissolved in 2 liters of boiling 95% ethanol and 50 g (0.24 mole) of p-toluene sulfonyl hydrazide added with vigorous stirring. The reaction mixture is cooled to room temperature, filtered and the solid washed with 95% ethanol. The solid is air dried to give 67.4 g (88%) with m.p. 225° (d).

III. Preparation of 3-Diazo-5-chloro-oxindole

Thirty-two grams (0.0902 mole) of the 3-p-tosylhydrazone of 5-chloro-isatin is suspended in 1.5 liters of dichloromethane and 0.90 liter of 0.2 N aqueous sodium hydroxide. The reaction mixture is stirred vigorously at room temperature for 1 hour and then at 41° for 2.5 hours. After cooling to room temperature the product is filtered off, washed well with water and air dried to give 10.7 g of crystals, m.p. 216°-218° (d).

The dichloromethane layer of the filtrate is separated, dried with sodium sulfate and stripped to give 4.4 g more of the title compound, m.p. 216°–218° (d), total yield 87%.

IV. Preparation of 9-chloro-5,6-dihydro-5-oxopyrazolo[1,5-c]quinazoline-2-carboxylic acid, ethyl ester Seven and one-half g (0.039 mole) of 3-diazo-5-chloro-oxindole and 8.4 g (0.086 mole) of ethyl propiolate are dissolved in 400 ml of xylene and heated to reflux (under nitrogen) for 1.5 hours, during which time a copious amount of solid forms. The reaction mixture is cooled to room temperature, filtered, washed with ether and dried to give 10 g (88% yield) of TLC pure material. This is crystallized from chloroform/methanol (4:1) and then from methanol to give 8.1 g of analytically pure compound.

An oral syrup is prepared as described below.

| Ingredient | Amount |
| --- | --- |
| 9-chloro-5,6-dihydro-5-oxopyrazolo-[1,5-c]quinazoline-2-carboxylic acid, ethyl ester | 500 mg |
| Sorbitol solution (70% N.F.) | 40 ml |
| Sodium benzoate | 150 mg |
| Sucaryl | 90 mg |
| Saccharin | 10 mg |
| Red Dye (F.D. & Co. No. 2) | 10 mg |
| Cherry flavor | 50 mg |
| Distilled water    qs to | 100 ml |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

The above compound is subjected to rat PCA testing as disclosed in Example 2. The following test results are obtained which indicate that the test compound has anti-asthma activity.

TABLE V

Results of Testing of 9-Chloro-5,6-dihydro-5-oxopyrazolo[1,5-c]-quinazoline-2-carboxylic acid, ethyl ester

| | | |
| --- | --- | --- |
| A. $ID_{50}$, mg/kg, rats dosed ten min. prior to challenge | IP | 9 |
| B. Maximum % inhibition rats dosed ten min. prior to challenge | IP (75 mpk) | 93% |

EXAMPLES 11 to 17

In accordance with the procedure outlined in Examples 1 and 2, the following compounds are prepared and tested and are shown to have anti-asthma activity.

TABLE VI

| Ex. No. | $R^1$ | $R^2$ | $R^3$ | $R^4$ | $R^5$ | Route/Dose(mpk) | % Inhibition | $ID_{50}$(mpk) |
| --- | --- | --- | --- | --- | --- | --- | --- | --- |
| 11. | $CH_3OC(=O)$ | $CH_3OC(=O)$ | H | H | H | IP/150 | 21 | — |
| 12. | H | $CH_3C(=O)$ | H | H | H | IP/75 | 32 | — |
| 13. | H | COOH | H | H | H | IP/75 | 36 | — |
| 14. | H | $CH_3C(=O)$ | $CH_3$ | H | H | IP/150 | 32 | — |
| 15. | $CH_3$ | $C_2H_5OC(=O)$ | H | H | H | IP/150 | 63 | 58 |
| 16. | H | $C_6H_5C(=O)$ | H | H | H | IP/150 | 37 | — |
| 17. | H | $C_2H_5OC(=O)$ | H | 9-$CH_3O$ | H | IP/25 | 90 | — |

EXAMPLE 18

Inhalation Formulation

The compositions which may be administered by inhalation as a fog or mist can be prepared and containers filled with them by the procedure that follows.

A suitable measured quantity of a medicament embraced by Formula I is mixed with, and dissolved in, a measured amount of co-solvent (e.g., ethanol, diethyl ether, etc.).

A measured quantity of the resulting solution is then introduced into an open container, which is then cooled to a temperature below the boiling point of the non-toxic propellant to be employed, a temperature of about −32° C. being satisfactory. A measured quantity of the liquefied propellant (e.g., dichlorodifluoromethane, dichlorotetrafluoroethane, etc.), cooled below its boiling point, is then introduced into the container and mixed with the solution already present. The quantities of the compounds introduced into the container are calculated to provide the desired concentration of each in the final composition. Without permitting the temperature of the container and its contents to rise above the boiling point of the propellant, the container is sealed with a closure equipped with a suitable dispensing valve arrangement. Upon warming to room temperature, the contents of the container is mixed by agitation to insure complete solution of the medicament; the sealed container is then ready to dispense the composition and provide the medicament of Formula I in aerosol form.

It is desirable to enclose the medicament of Formula I in a pressure-tight container having a suitable outlet valve secured in an opening in the top wall of the container. Glass bottles can be substituted for metal containers, thereby making it possible to readily observe the amount of medicament remaining therein. The glass bottle can be coated with a clear plastic film as a safety measure. A dip-tube of suitable material can be connected with the opening containing the valve arrangement and extending to the bottom of the container, or an inverted system without a dip-tube can be employed. Upon opening the valve, the composition is expelled through the opening in the form of a fine stream to form an aerosol of the medicament of Formula I. To accomplish suitable aerosolization of the medicament, the opening is preferably constructed to provide a small orifice so as to expel a fine spray (e.g., a fog or mist) of the composition. The thus described container is typical of the class known as an "aerosol" (bomb).

What is claimed is:

1. A method of preventing the symptoms of asthma in a mammalian host in need of such treatment, which comprises administering to a mammalian host a prophylactically effective amount of a compound of the structure 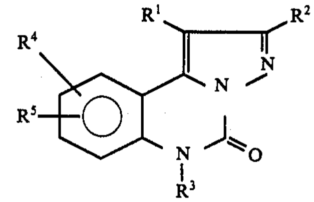 wherein $R^1$ is hydrogen, lower alkoxycarbonyl, lower alkyl, phenyl optionally substituted with halogen, lower alkyl or lower alkoxy, $R^2$ is lower alkoxycarbonyl, carboxyl, acetyl, hydrogen, lower alkyl, benzoyl or monosubstituted benzoyl in which the substituent is fluoro, chloro, bromo, lower alkyl, or lower alkoxy; and $R^3$ is hydrogen, methyl, benzyl, phenyl or monosubstituted phenyl or monosubstituted benzyl in which the substituent is fluoro, chloro or bromo; $R^4$ and $R^5$ may be the same or different and may be hydrogen, lower alkyl, lower alkoxy, F, Cl or Br or pharmaceutically acceptable salts thereof, dispersed in a non-toxic physiologically acceptable carrier.

2. The method as defined in claim 1 where in said compound $R^2$ is carboxyl or lower alkoxycarbonyl.

3. The method as defined in claim 1 wherein said compound is 5,6-dihydro-5-oxopyrazolo[1,5-c]quinazoline-2-carboxylic acid, ethyl ester.

4. The method as defined in claim 1 wherein said compound is pyrazolo[1,5-c]quinazolin-5(6H)-one.

5. The method as defined in claim 1 wherein said compound is administered parenterally.

6. The method as defined in claim 1 wherein said compound is administered orally.

7. The method as defined in claim 1 wherein said compound is administered in an amount within the range of from about 0.1 to about 500 mg per kg of body weight per day.

* * * * *